United States Patent [19]
McIntosh, Jr. et al.

[11] Patent Number: 4,908,209
[45] Date of Patent: Mar. 13, 1990

[54] BIOCIDAL DELIVERY SYSTEM OF PHOSPHATE ESTER AND METHOD OF PREPARATION THEREOF

[75] Inventors: Robert H. McIntosh, Jr., Greensboro, N.C.; Albin F. Turbak, Sandy Springs, Ga.; Robert H. McIntosh, Sr., Greensboro, N.C.

[73] Assignee: Interface, Inc., Atlanta, Ga.

[21] Appl. No.: 190,370

[22] Filed: May 5, 1988

Related U.S. Application Data

[63] Continuation-in-part of Ser. No. 47,561, Apr. 27, 1987, which is a continuation-in-part of Ser. No. 781,710, Oct. 2, 1985, which is a continuation-in-part of Ser. No. 635,728, Oct. 9, 1984, abandoned, which is a continuation-in-part of Ser. No. 713,445, Mar. 19, 1985, abandoned, which is a continuation-in-part of Ser. No. 736,652, May 21, 1985, Pat. No. 4,647,601, which is a continuation-in-part of Ser. No. 744,730, Jun. 13, 1985, abandoned, which is a continuation-in-part of Ser. No. 570,952, May 21, 1985, and a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned.

[51] Int. Cl.$^4$ .................... A01N 25/08
[52] U.S. Cl. .................... 424/409; 424/78; 424/81; 424/83; 424/408; 424/418; 424/419; 514/76; 523/122
[58] Field of Search .................... 424/489, 78, 491, 499, 424/501, 456, 81, 83, 408, 409, 418, 419; 523/122; 514/76, 143, 148

[56] References Cited

U.S. PATENT DOCUMENTS

| | | | |
|---|---|---|---|
| 2,202,124 | 5/1940 | Tattersal | 106/18.17 |
| 2,272,668 | 2/1942 | Honel | 558/113 |
| 2,337,424 | 12/1943 | Stoner et al. | 260/86 |
| 2,490,100 | 12/1949 | Smith | 523/122 X |
| 2,541,088 | 2/1951 | Nikawitz | 260/584 |
| 2,552,325 | 5/1951 | Kosolapoff | 260/461 |
| 2,592,564 | 4/1952 | Hardman | 106/273 |
| 2,676,122 | 4/1954 | McCarthy | 117/139.5 |
| 2,756,175 | 7/1956 | Goldstein et al. | 167/33 |
| 2,818,364 | 12/1957 | Birum | 514/148 X |
| 2,831,782 | 4/1958 | Zvanut | 117/127 |
| 2,872,351 | 2/1959 | Wedell | 117/121 |
| 2,891,878 | 6/1959 | Chamberlain | 428/421 |
| 2,922,738 | 1/1960 | McDermott et al. | 167/22 |
| 2,935,490 | 5/1960 | Havens et al. | 260/45.7 |
| 2,960,529 | 11/1960 | McCall et al. | 260/461 |
| 2,970,081 | 1/1961 | McCall et al. | 167/30 |
| 2,976,186 | 3/1961 | Thompson et al. | 260/45.8 |
| 2,997,454 | 8/1961 | Leistner et al. | 260/45.8 |
| 3,116,201 | 12/1963 | Whetstone et al. | 514/148 X |
| 3,130,505 | 4/1964 | Markevitch | 523/122 X |
| 3,179,676 | 4/1965 | Stern, Jr. | 523/122 X |
| 3,212,967 | 10/1965 | McFadden et al. | 523/122 X |
| 3,247,134 | 4/1966 | Hwa et al. | 260/2.5 |
| 3,267,149 | 8/1966 | Garner | 523/122 X |
| 3,279,986 | 10/1966 | Hyman | 167/42 |
| 3,280,131 | 10/1966 | Wakeman et al. | 260/286 |
| 3,294,775 | 12/1966 | Wasserman | 260/100 |
| 3,308,488 | 3/1967 | Schoonman | 5/355 |
| 3,312,623 | 4/1967 | Fitch et al. | 252/106 |
| 3,364,192 | 1/1968 | Leach | 260/94.9 |
| 3,402,240 | 9/1968 | Cain et al. | 514/148 X |
| 3,404,140 | 10/1968 | Fukumoto et al. | 260/93.7 |
| 3,423,482 | 1/1969 | Katsumura et al. | 523/122 X |
| 3,428,713 | 2/1969 | Bartlett et al. | 260/924 |
| 3,437,721 | 4/1969 | Baranauckas et al. | 523/122 X |
| 3,475,204 | 10/1969 | Patterson | 117/138.8 |
| 3,498,969 | 3/1970 | Lewis | 260/211 |
| 3,527,726 | 9/1970 | Gower et al. | 260/29.6 |
| 3,577,515 | 5/1971 | Vandegaer | 424/32 |
| 3,620,453 | 11/1971 | Gancberg et al. | 239/60 |
| 3,639,583 | 2/1972 | Cardarelli et al. | 523/122 X |
| 3,639,594 | 2/1972 | Notarianni et al. | 514/76 |
| 3,641,226 | 2/1972 | Partridge et al. | 260/990 |
| 3,671,304 | 6/1972 | Mischutin | 117/138 |
| 3,705,235 | 12/1972 | McIntosh et al. | 424/83 |
| 3,708,573 | 1/1973 | Yoshinaga et al. | 260/29.6 |
| 3,714,256 | 1/1973 | Samour et al. | 260/29.6 |
| 3,758,283 | 9/1973 | Matt | 44/62 |
| 3,762,415 | 10/1973 | Morrison | 128/290 |
| 3,769,377 | 10/1973 | De Selms | 260/958 |
| 3,776,806 | 12/1973 | Mayer et al. | 161/88 |
| 3,793,408 | 3/1974 | Schulz | 260/990 |
| 3,819,656 | 6/1974 | Barie, Jr. et al. | 260/343.7 |
| 3,873,648 | 3/1975 | Balde | 260/990 |
| 3,885,000 | 5/1975 | Beriger et al. | 260/956 |
| 3,888,978 | 6/1975 | Duwel et al. | 424/199 |
| 3,896,101 | 7/1975 | McIntosh et al. | 260/93.7 |
| 3,897,491 | 7/1975 | Toy et al. | 523/122 X |
| 3,897,521 | 7/1975 | Beriger et al. | 260/948 |
| 3,919,410 | 11/1975 | McIntosh et al. | 424/78 |
| 3,920,836 | 11/1975 | McIntosh et al. | 424/315 |
| 3,925,442 | 12/1975 | Samour | 424/315 |
| 3,928,563 | 12/1975 | McIntosh et al. | 424/78 |

(List continued on next page.)

FOREIGN PATENT DOCUMENTS 1162356 2/1984 Canada.
0018492 11/1980 European Pat. Off..

(List continued on next page.)

OTHER PUBLICATIONS

Yuan et al., *Phosphorus and Sulphur*, vol. 18, 323–326 (1983).

(List continued on next page.)

*Primary Examiner*—Thurman K. Page
*Attorney, Agent, or Firm*—Kilpatrick & Cody

[57] ABSTRACT

A biocidal phosphate ester in combination with an inert inorganic or organic particulate or polymeric carrier. The biocidal-carrier composition is useful in extending the effective lifetime of the biocidal phosphate ester when incorporated into a variety of materials including plastics, fibrous materials, and solutions. Applications of the disclosed carrier compounds include preparation of mildew resistant paints and plastics having extended antimicrobial properties despite extensive washing and wear of the surface.

22 Claims, No Drawings

U.S. PATENT DOCUMENTS

| | | | |
|---|---|---|---|
| 3,932,612 | 1/1976 | Burkhardt et al. | 424/78 |
| 3,933,947 | 1/1976 | Kishino et al. | 260/949 |
| 3,959,556 | 5/1976 | Morrison | 428/364 |
| 3,972,243 | 8/1976 | Driscoll et al. | 74/200 |
| 3,979,307 | 9/1976 | Kolaian et al. | 252/8.75 |
| 3,991,187 | 11/1976 | Hogberg et al. | 514/76 |
| 4,004,001 | 1/1977 | Large et al. | 424/200 |
| 4,006,204 | 2/1977 | Rajadhyaksha et al. | 260/958 |
| 4,024,324 | 5/1977 | Sparks | 526/2 |
| 4,025,583 | 5/1977 | Mead et al. | 260/925 |
| 4,039,636 | 8/1977 | Claus et al. | 260/963 |
| 4,071,552 | 1/1978 | Ferland et al. | 260/562 R |
| 4,083,860 | 4/1978 | Ruf | 260/403 |
| 4,094,970 | 6/1978 | Behrenz et al. | 424/78 |
| 4,107,292 | 8/1978 | Nemeth | 424/78 |
| 4,110,504 | 8/1978 | Hull et al. | 428/97 |
| 4,119,724 | 10/1978 | Thizy et al. | 424/45 |
| 4,139,616 | 2/1979 | Ducret et al. | 424/222 |
| 4,152,421 | 5/1979 | Tsutsumi et al. | 424/57 |
| 4,165,369 | 9/1980 | Watanabe el al. | 71/93 |
| 4,235,733 | 11/1980 | Watanabe et al. | 252/107 |
| 4,259,078 | 3/1981 | Kleber et al. | 8/188 |
| 4,272,395 | 8/1981 | Wright | 424/70 |
| 4,276,418 | 6/1981 | Howarth | 544/243 |
| 4,289,634 | 9/1981 | Lewis et al. | 252/32.5 |
| 4,343,853 | 8/1982 | Morrison | 428/233 |
| 4,361,611 | 11/1982 | Schafer et al. | 428/96 |
| 4,363,663 | 12/1982 | Hill | 523/122 X |
| 4,401,712 | 8/1983 | Morrison | 428/289 |
| 4,432,833 | 2/1984 | Breese | 162/138 |
| 4,442,095 | 4/1984 | Johnston | 544/120 |
| 4,442,096 | 4/1984 | Johnston | 424/250 |
| 4,560,599 | 12/1985 | Regen | 428/36 |
| 4,598,006 | 7/1986 | Sand | 424/81 |
| 4,647,601 | 3/1987 | McIntosh | 523/122 |
| 4,661,477 | 4/1987 | Privitzer et al. | 514/76 |
| 4,770,694 | 6/1987 | Iwasaki et al. | 252/106 |

FOREIGN PATENT DOCUMENTS

| | | |
|---|---|---|
| 0035375 | 9/1981 | European Pat. Off. . |
| 1228031 | 11/1966 | Fed. Rep. of Germany . |
| 2530584 | 1/1977 | Fed. Rep. of Germany . |
| 3014765 | 10/1981 | Fed. Rep. of Germany . |
| 3039437 | 5/1982 | Fed. Rep. of Germany . |
| P3248708.8 | 7/1984 | Fed. Rep. of Germany . |
| 48-28058 | 8/1973 | Japan ... 514/148 |
| 50-157531 | 12/1975 | Japan ... 514/148 |
| 53-081577 | 7/1978 | Japan . |
| 55-004347 | 1/1980 | Japan ... 514/143 |
| 2157952A | 11/1985 | Japan . |
| 617854 | 6/1980 | Switzerland . |
| 1122664 | 11/1984 | U.S.S.R. . |
| 1036578 | 7/1966 | United Kingdom . |
| 1302894 | 1/1973 | United Kingdom . |
| 2042574 | 9/1983 | United Kingdom . |
| 2131029 | 1/1986 | United Kingdom . |

OTHER PUBLICATIONS

Nakamura, *Journal of Radioanalytical Chemistry*, 52 (2), 343–354 (1979).

Nakamura, *Journal of Radioanalytical Chemistry*, 44, 37–47 (1978).

Partridge et al., *J. Inorg. Nucl. Chem.*, 31, 2587–2589 (1969).

Tachimori et al., *Journal of Radioanalytical Chemistry*, 67 (2), 329–337 (1981).

Honaker et al., *J. Inorg. Nucl. Chem.*, 39, 1703–1704 (1977).

J. Perka et al., *Tenside Detergents*, 15, 295–298 (1978) 6.

Sorbe et al., *Quim. Apl. Jorn. Com. Esp. Deterg.*, 11th, 415–430 (1980).

Yoshihira Koda et al., "The Synthesis of Surfactant and the Use Thereof", pp. 96–99 and 436–447 (1977).

Takehiko Fujimoto, "Introduction in New Surfactant", pp. 295–297 (1974).

*J. Inorg. Nucl. Chem.*, 38, 2127–2129 (1976).

Matsui et al., *Chem. Abstracts*, 82, 141561 (1974) (JP 74 24,806).

Ogasawara et al., *Chem. Abstracts*, 81, 107078f (1974) (U.S. Pat. No. 3,799,904).

Hall et al., *Chem. Abstracts*, 80, 123000 (1973), *ASLE Trans.* 16(4), 291–296.

Keil et al., *Chem. Abstracts*, 76, 101944k (1972), Ger. Offen. 2,030,256.

Sudakova et al., *Chem. Abstracts*, 70, 56711v (1969) (USSR 229,879).

Gialkdi et al., *Chem. Abstracts* 43, 6363a (1949) (*Farm. sci. e tec.*, 4), 166–175.

Tak Chemicals Ltd., 1580026 (Jun. 1977).

McCoy, *Microbiology of Cooling Water*, 94–95 (Chemical Pub. Co., NY, 1980).

BIOCIDAL DELIVERY SYSTEM OF PHOSPHATE ESTER AND METHOD OF PREPARATION THEREOF

This application is a continuation-in-part to U.S. Ser. No. 047,561, filed Apr. 27, 1987, entitled "Microbiocidal Composition and Method of Preparation Thereof" by Robert H. McIntosh, which is a continuation-in-part of U.S. Ser. No. 781,710 filed Oct. 2, 1985; U.S. Ser. No. 635,728 filed Oct. 9, 1984, now abandoned; U.S. Ser. No. 713,455 filed Mar. 19, 1985, now abandoned; U.S. Ser. No. 736,652 May 21, 1985, now U.S. Pat. No. 4,647,601; U.S. Ser. No. 744,730 filed Jun. 13, 1985, now abandoned; all of which are continuations-in-part of U.S. Ser. No. 570,952 filed Mar. 8, 1984, a continuation of U.S. Ser. No. 523,734 filed Aug. 16, 1983, now abandoned, which is a continuation of U.S. Ser. No. 226,006 filed Jan. 19, 1981, now abandoned, which is a continuation of U.S. Ser. No. 930,879 filed Aug. 4, 1978, now abandoned.

TECHNICAL FIELD

The present invention relates to biocidal compositions and methods for their delivery.

BACKGROUND

Bacteria, fungi, viruses, algae and other microorganisms are always present in our environment. Such microorganisms are frequently an essential part of ecological systems, industrial processes, and healthy human and animal bodily functions, such as digestion. In other instances, however, microorganisms are highly undesirable as a cause of illness, odors and damage or destruction of a wide variety of materials.

The species and numbers of microorganisms present vary depending on the general environment, on the nutrients and the moisture available for the growth of the microorganisms, and on humidity and temperature of the local environment. Nutrients for microorganisms abound in the normal environment. Furthermore, many materials, including plastic coatings and objects, wood, paper and other natural fibers can serve as nutrients for microorganisms which will degrade those materials. In addition, certain bacteria are capable of remaining viable in a dormant state on floors or on objects for long periods of time until they are deposited in the proper media for growth. Consequently, potentially harmful microorganisms can be transported merely by walking on floors, brushing against walls or furniture or by handling objects.

It is well recognized that a major difficulty in health care facilities is the spread of infectious diseases caused by a wide variety of microorganisms. The problem is exacerbated in these facilities because many of the patients are in a weakened condition or immunosuppressed. One of the most common means by which these organisms are spread is health care personnel. Another important source of infection are the floors, furniture and other plastic objects routinely used in these settings. Conventionally, the plastic products in these facilities are periodically cleaned with strong disinfecting cleansers to remove or kill accumulated microorganisms. Between cleanings, however, it is possible for the plastic products to constitute a major vector for cross-infection or spread of infections diseases.

Pathogenic microorganisms can also be deposited on fabrics such as towels, clothes, laboratory coats and other fabrics where they remain viable for long periods of time. When the microorganisms grow on or in a plastic product, fiber, or fabric, they form unsightly colonies and can eventually break down the plastic, fiber, fabric, or other material. Washing with conventional detergents does not always kill or remove the microorganisms.

The control of microbial growth is a major problem in both industry and the home. It has proved difficult, however, to develop a microbiocidal composition that is effective in controlling the growth of a wide variety of unwanted microorganisms and is, at the same time, safe for use around human beings and animals. Another difficulty is the extreme variability of response of various microorganisms to conventional microbiocidal agents. Even within bacteria, Gram-negative and Gram-positive bacteria respond differently to antibiotics. Further, the antibiotics that are effective against procaryotic organisms are usually ineffective against eucaryotic microorganisms such as fungi and yeasts.

U.S. Ser. No. 047,561 entitled "Microbiocidal Composition and Method of Preparation" filed Apr. 27, 1987 by Robert H. McIntosh disclosed a broad spectrum, safe, biocidal composition having the following general formula:

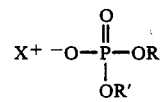

wherein R and R' are an alkyl, aryl, aralkyl or alkaryl group, one of R or R' can be H, X is a Group I metal ion, Group II metal ion, transition metal ion, or an organic ion such as an ammonium ion, and there is at least one free hydroxyl group. Examples of the alkyl, aryl, aralkyl and alkaryl include straight chains, branched chains or cyclic alkyl groups having from 2 to 24 carbon atoms, polyoxyethylene or polyoxypropylene having from 2 to 12 ethylene oxide or propylene oxide units respectively, alkyl phenoxy polyoxyethylene containing from 2 to 12 ethylene oxide units, alkyl phenoxy polyoxyethylene containing ethylene oxide units and from 2 to 24 carbon atoms in the phenolic alkyl chain, or a polyhydroxy compound such as ethylene glycol, glycerol, or sorbitol. The positively charged ion does not appear to be essential for biocidal activity against all types of organisms, although the charge of the phosphate ester does affect the degree of biocidal activity. The relative ratios of mono-and di-esters also appears to affect the antimicrobial activity. As used herein, the general compound is referred to as a "phosphate ester". When the salt is specifically required or utilized, the compound is referred to as a "phosphate ester salt".

This compound has previously been demonstrated to be effective when incorporated into epoxy resins, combined with a surfactant for use as an antimicrobial detergent, used as a coating for fabric, wood or plastics, or a preservative when applied to an absorbent material. Despite the successful use of these compounds in a variety of ways, there remains a need for a means of incorporating the compounds into polymeric materials which results in effective antimicrobial control over an extended period of time, wherein the unbound phosphate ester or salt is not extensively removed by washing and surface wear. Further requirements for such a system are that it cannot decrease the stability and biocidal activity of the phosphate compounds.

Accordingly, it is an object of the present invention to provide the biocidally effective phosphate esters in combination with carrier materials to yield products having biocidal properties which are resistant to washing and wear over an extended period of time.

Another object of the present invention is to provide methods for incorporating the biocidally effective phosphate esters into carrier materials which are relatively easy and inexpensive.

A further object of the present invention is to provide methods and means for the application of the biocidally effective phosphate esters to the surface of both synthetic and natural fibers, fabrics and fibrous surfaces to thereby impart biocidal properties to the materials which are resistant to washing.

SUMMARY OF THE INVENTION

The present invention includes methods to incorporate a biocidal compound having the general formula

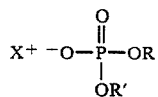

wherein R and R' are an alkyl, aryl, aralkyl or alkaryl group, one of R or R' can be H, X is a Group I metal ion, Group II metal ion, transition metal ion, or an organic ion such as an ammonium ion, and there is at least one free hydroxyl group. This compound, while more accurately termed a phosphoric acid, is described herein as a "phosphate ester" or salt thereof.

In the preferred embodiment, the biocidal compound is incorporated onto the surface, or absorbed within the structure, of a carrier material. Examples of carrier materials include diatomaceous earth or other high-surface area particulate inert materials, polymers which can bind the phosphate ester such as cationic synthetic resins and natural polymers, for instance, chitin, gelatin and collagen having quarternary amine sites or free amine functions, and polymeric microcapsules.

In one embodiment, the biocidal compound is adsorbed onto diatomaceous earth to provide a dusting powder with slow release of the biocidal compound. In another embodiment, the biocidal compound is adsorbed onto a powder such as celite for use as an additive to house paint to retard decomposition of the paint due to mold or bacterial growth. In yet another embodiment, the biocidal compound is mixed with or bound to a cationic resin or monomers which can be subsequently polymerized for use, for example, as a preservative of canvas used for outdoor activities. The biocidal compound can also be bound to polymers for use in wound coverings or filtration of either air or liquid. In still another embodiment, the biocidal compound is microencapsulated within a polymer structure from which it is released by exposure to agents such as ultrasound, temperature, chemical agents, or degradation over time.

Other agents can be combined with the biocidal compound and carrier, taking care that the compound is not completely neutralized, which can lead to loss of biocidal activity, especially activity against Gram-negative bacteria. For example, a buffering agent can be added to protect against complete neutralization of the biocidal compound. Surfactants, colorings, and a variety of other materials can also be combined with the biocidal compound.

DETAILED DESCRIPTION OF THE INVENTION

The present invention relates to delivery systems for a biocidal and insecticidal phosphate ester compound. The compound is the subject of U.S. Ser. No. 047,561 filed Apr. 27, 1987 by Robert H. McIntosh entitled "Microbiocidal Composition and Method of Preparation Thereof". These compounds are normally viscous liquids.

The biocidal compound is incorporated onto or into a carrier material in order to provide a mechanism for continued release of the biocidal compound over an extended period of time following incorporation or application to another object or material. By utilizing the described carrier materials, one is able to obtain a sustained release over an extended period of time despite washing of the object or wearing away of the immediate surface. At the same time, selection of the appropriate carrier material ensures that the compound is released in a controlled fashion over a period of time. The phosphate ester-carrier mixture is also useful as a means by which the compound can be added to materials where the liquid phosphate ester causes unacceptable alteration of the viscosity or mechanical properties of the material.

Carrier materials include inert, porous particulate materials, cationic resins, proteins having free amine functions, and polymeric microcapsules.

Examples of inert particulate materials are diatomaceous earth, attapulgite clays, colloidal silicas, zeolite solids, and vermiculite. There are several forms of diatomaceous earth, including celite and a less porous form known as "silica flour". The phosphate ester-carrier composition can also be mixed into thermoplastic polymers such as polyesters and extruded as films or fibers using mixing and extruding techniques known to those skilled in the art. The films and fibers can be fragmented for use as fillers or filter packing. Examples of useful polymers include polyolefins, polystyrenes, polyamines, polyacrylics, polyamides, polyethers, and polyurethanes. Care must be exercised in the selection of the polymeric or particulate material to avoid complete neutralization of the charge on the phosphate ester.

Natural and synthetic polymers having an actual or incipient positive charge can be reacted with the phosphate ester. For example, the phosphate ester can be bound to naturally occurring polysaccharide and protein polymers such as acetylated 2-amino cellulose (chitin), chitosan (the hydrolyzed form of chitin), gelatin, and collagen. The phosphate ester binds to the 2-amino position of the chitin. A microfibrillated form of chitin and chitosan, produced by passing solid slurries of these materials through a Manton-Gaulin homogenizer, obtained from Diacel, Japan, is effective as a carrier of the phosphate ester compound. Gelatin, a heterogeneous mixture of water soluble proteins of high average molecular weight, is prepared by hydrolysis of collagen. Gelatin forms a salt with the phosphate ester compound. Collagen reacts in a similar fashion with the phosphate ester compound. When either gelatin or collagen is mixed with the biocidal phosphate ester and heated, a film forms containing the phosphate compound. This film can be used as a biocidal coating for fibers of animal or plant origin, including wound bandages, tissues, and air filters.

The phosphate ester is microencapsulated for applications requiring more controlled release. Numerous methods and materials for microencapsulation or coacervation are known to those skilled in the art. In one method, small beads of the phosphate ester compound are prepared by simultaneously spraying polymer and phosphate derivatives through concentric nozzles. Alternatively, the phosphate ester is encapsulated by coacervation. Up to 50% by weight of liquid phosphate ester is dispersed in a gelatin, guar gum or polymer solution and the polymer precipitated around the phosphate ester by addition of a weak acid.

The microencapsulated phosphate ester is released as a function of time, environment, wear, or exposure to a specific agent such as ultrasound, light, or a chemical compound.

Exposure to strong bases such as sodium or potassium hydroxide can completely neutralize the compound, thereby abolishing the anti-Gram negative bacterial activity of the phosphate ester compound. It is therefore desirable to protect the compound against exposure to strong basic materials. A preferred means for protecting the phosphate ester is to incorporate a buffering agent into the carrier material. Examples of acceptable buffering agents include sodium phosphate/phosphoric acid, potassium biphthalate, potassium citrate, and sodium acetate/acetic acid, and sodium citrate/citric acid. The buffered solutions can be mixed with a carrier as described before and sprayed directly onto a surface to inhibit or destroy bacteria and fungus. The buffer prevents inactivation of the phosphate ester by the salts in the surfaces which may leach out from the surface. For example, buffered solutions are preferred for use in applying the phosphate ester compound to brick walls, cement bridges, outside cinder block foundations and other materials where mold prevention is desirable but inactivating salts may leach out of the surface material.

The phosphate ester can also be mixed with a nonionic detergent, wax, or oil before adsorption onto the carrier. These compounds are useful in protecting the antimicrobial agent as well as in delaying release.

The biocidal compound described in U.S. Ser. No. 047,561 filed Apr. 27, 1987 is a phosphate ester and the salt thereof. In the preferred embodiment, the phosphate ester is partially neutralized with an organic substituted amine to produce an ammonium salt of a phosphoric acid. The phosphate esters can instead be partially neutralized using zinc acetate, magnesium acetate, sodium hydroxide or potassium hydroxide (Group IA metals, Group IIA metals, and transition metals). Selection of the positive ion does affect biocidal activity, principally the anti-Gram negative bactericidal activity, although the phosphate ester appears to be the primary source of biocidal activity. The biocidal activity is also a function of the relative ratio of mono-to di-alkyl substituted phosphoric acid ester and the charge on the phosphate molecule due to the available OH- groups.

In a preferred method, the biocidal phosphate ester is prepared by reacting 1 mole of phosphorous pentoxide with 3 moles of alcohol, most preferably 2-ethylhexanol, at a temperature of between about 60° C. and 120° C. The phosphorous pentoxide is slowly added to the alcohol while the mixture is aggitated. Completion of the reaction is determined by titration of the resulting acid with a solution of potassium or sodium hydroxide. The reaction products include dialkyl phosphoric acid and monoalkyl phosphoric acid.

Anti-microbiocidal activity is tested by plating a microorganism onto Trypticase Soy Nutrient Agar, or other appropriate media, punching 6 mm diameter, 5 mm deep holes into the agar, and applying 0.05 ml of each of the undiluted test compounds into the holes. The petri dish is examined for growth of the microorganisms after incubation for 24 hours at 30° C. The diameter of the clear area surrounding the hole containing the compound being tested is indicative of the degree of antimicrobiocidal activity.

To form the ammonium salt of the phosphate ester compound, one mole each of the reaction products of the phosphorous pentoxide and alcohol (assuming 50% monoalkyl and 50% dialkyl phosphoric acid is produced in the reaction) is partially neutralized with 1.3 moles of an amine such as bis(hydroxyethyl) cocoamine by heating the mixture at a temperature between 60° C. and 120° C. until the reaction is complete.

Metal salts of the phosphate ester are prepared by mixing a metal salt such as magnesium acetate or zinc acetate with an alkyl phosphate, such as 2-ethylhexyl phosphate (or (2-ethylhexyl)phosphoric acid according to IUPAC), warming to dissolve, and vacuum stripping off the acetic acid, then testing for activity.

For example, salts of an alkyl phosphate ester were prepared by mixing either a Group I metal, magnesium, or a transition metal, zinc, with an alkyl phosphate ester, then testing for antimicrobial activity, as follows.

| | |
|---|---|
| 1. Magnesium (acetate)$_2$ .4 $H_2O$ | 20 gram |
| 2-ethyl-hexyl phosphate (Rockmart) | 53 gram |
| 2. Zinc (acetate)$_2$ .2 $H_2O$ | 15 gram |
| 2-ethyl-hexyl phosphate (Rockmart) | 53 gram |

The process was the same for both products: mix the metal salt with the 2-ethylhexyl phosphate, warm to dissolve the metal acetate and after dissolution, vacuum strip off the acetic acid.

The resultant products are clear, colorless, viscous liquids.

The magnesium phosphate and zinc phosphate compounds were washed and evaluated for biocidal activity using the standard cup method test procedure:

A sterile nutrient agar solution was prepared. The nutrient agar was inoculated with a 24 hour culture of either *Staphylococcus aureus* (Gram positive) or *Pseudomonas aeruginosa* (Gram negative) organisms. The inoculated agar was poured into 100×15 mm sterile petri dishes and allowed to solidify at room temperature. After solidifying small reservoirs were punched for the compounds to be tested. Magnesium phosphate was added to one well and zinc phosphate was added to another. The plates were then incubated 24 hours at 30° C. and examined for zones of inhibition.

The zone of inhibition of Staphylococcus was 15 mm for the magnesium phosphate and 19 mm for the zinc phosphate. No inhibition of the Pseudomonas was observed, however, the results clearly demonstrate that Group II and transition metal salts of the alkyl phosphate esters have bactericidal activity.

EXAMPLE I

Preparation of Biocidal Powders from Diatomaceous Earth using Ammonium Salts of Phosphoric Acid Esters A biocidal alkyl phosphate powder was prepared by reacting a fatty or hydroxy amine, bis(hydroxyethyl)-cocoamine, with the phosphate esters to form the ammonium salt which was then mixed with diatomaceous earth.

33 grams of partially neutralized monophosphate ester and diphosphate ester prepared by reaction of $P_2O_5$ with 2-ethylhexanol followed by reaction with dimethylcocoamine were mixed with 33 grams of a less viscous predominantly monophosphate ester mixture and then added to 33 grams of celite (diatomaceous earth) obtained from the John Manville Corporation. This was stirred for 1 hour to yield a free flowing powder having 66% by weight active phosphate ester which is useful as an antimicrobial dusting powder. This powder was subsequently used in example II.

Similar results were obtained by mixing 50 grams of esters with 50 grams of celite.

A biocidal alkyl phosphate powder was prepared by adding 50 grams of monoalkyl phosphoric acid to 50 grams of hexane. This solution was slurried with 50 grams of celite. The hexane was evaporated from the slurry with stirring to yield a free flowing powder containing 50% by weight of adsorbed phosphate ester.

These powders were tested for antimicrobial activity and found to inhibit both Staphylococcus and Psuedomonas.

EXAMPLE II

Preparation of an Anti-microbial Latex Paint 90 grams of 66% phosphate ester-33% diatomaceous earth prepared in example I (equivalent to about 2 oz. of undiluted phosphate ester salt) was mixed into one gallon of latex interior housepaint and applied to the interior walls of a bedroom. In contrast to results obtained with latex paint in the absence of the phosphate ester, the painted walls remained free of mildew for two years even in high humidity.

By adsorbing the phosphate ester onto the diatomaceous earth prior to addition to the paint, there was only a slight change in the viscosity of the latex paint. When the same amount of compound was added directly to the latex paint, the paint underwent a pronounced change of viscosity and lost some of its smooth flow and spreading characteristics.

EXAMPLE III

Biocidal Synthetic Polymeric Coatings

One mole of mono 2-ethylhexyl phosphoric acid, a very active anti-microbiocidal agent, was partially neutralized with approximately 1 mole of dimethylaminoethyl methacrylate. The resulting ammonium salt can be added to a substrate such as nylon, polyester, or cloth for polymerization in the presence of a suitable catalyst (a peroxide such as potassium persulfate, dibenzoyl peroxide, methylethyl ketone peroxide, etc.) to produce a dimethylaminoethyl methacrylate polymer having the mono substituted phosphoric acid compound attached to it which is useful as a protective coating on fabric and fibers. The more hydrophobic the matrix material, the longer lasting the biocidal activity.

Similarly, one mole of 2-ethyl hexyl phosphate ester was partially neutralized with 1 mole of dimethylaminoethyl methacrylate prepared by esterification of methacrylic acid with dimethylaminoethanol. The resulting ammonium salt of the phosphate ester can be added to a porous or fibrous substrate, cotton, in the presence of a catalyst and polymerized in situ to form a protective coating.

EXAMPLE IV

Biocidal Natural Polymeric Coatings.

One gram of monophosphate ester can be added to a 3% solution of gelatin in water and also used as a protective coating for fabrics such as cotton or wool.

Similarly, 3 grams of biocidal phosphate ester can be mixed into a 3% gelatin solution in water and used to coat a glass wall type air filter for home furnace.

EXAMPLE V

Biocidal Gelatin Microcapsules.

50 grams of monophosphate ester can be vigorously mixed into a 3% gelatin solution using a homogenizer. The dispersion is then neutralized with diethylethanolamine. As the pH approaches the isoelectric point of the gelatin, approximately 5.5, the gelatin precipitates around the phosphate ester forming droplets containing the phosphate ester within a gelatin shell. These solidify into microcapsules.

Examples of buffering agents which can be included with the phosphate ester within the microcapsule include 0.1 M of potassium biphthalate-HCl pH 2.8, 0.1 M primary potassium citrate pH 3.7, 0.1 M acetic acid-sodium acetate pH 4.6, 0.1 M secondary sodium pH 5.0.

EXAMPLE VI

Biocidal Epoxy Matrices.

The biocidal properties of epoxy encapsulated monoalkyl amine phosphate ester/dialkyl amine phosphate ester, prepared by reacting two moles of the product of the reaction of $P_2O_5$ with 2-ethylhexanol with 1.3 moles of dimethylcocoamine, were significantly improved by adsorbing the phosphate ester salt to either celite diatomaceous earth from John Manville Co., United States or Silver Bond silica flour from Tammsco, Inc., Tams, IL., prior to incorporation into the epoxy. The phosphate ester salt-carrier is preferably mixed into the hardener or the mixture of the hardener and resin, rather than into the unpolymerized resin, to retain the maximum amount of biocidal activity.

The following mixtures were prepared using the phosphate ester salt-silica flour mixture and tested for biocidal activity:

|   |   |   | parts by weight |   | parts by weight |
|---|---|---|---|---|---|
| A. | epoxy resin | DER 331 | 56.7 | DER 331 | 55.81 |
|    | diluent | WC-8 | 5.0 | DER 732 | 6.25 |
|    | defoamer | Dehydran | 0.3 | Dehydran | 0.3 |
| B. | hardener | Epotuf | 27.3 | Epotuf | 26.95 |
|    | phosphate ester-carrier |  | 10.7 |  | 10.7 |

DER 331 is a DGEBPA epoxy resin, equivalent weight 182-190, obtained from Dow Chemical Co. DER 732 is a polyglycol diepoxide, equivalent weight 305-335, obtained from Dow Chemical Co. WC-8 is a $C_{12}$–$C_{14}$ alkylglycidyl ether, equivalent weight 280-300, obtained from Wilmington Chemical Co., Wilmington, DE. Dehydran 1208 is a defoamer sold by Henkel, Inc., Teaneck, NJ. Epotuf 37-606 is a polyamine epoxy aduct sold by Reichold Chemical Co., Inc., White Plains, NY.

The samples prepared from this formula were tested for biocidal activity and the activity compared with the activity for the phosphate ester salt-epoxy mixture alone, as described below. Significantly better results were obtained for the mixture with carrier than for the phosphate ester salt-epoxy mixture alone.

Preparation of epoxy coating for test:

Liquid epoxy material is poured into 100 mm diameter square plastic petri dishes to a depth of approximately 5 mm. One-half of the dishes contain epoxy plus phosphate ester, with or without carrier, (experimentals) and an equal number of dishes contain only epoxy (controls). Depth of epoxy has no effect on biocide activity at the epoxy surface.

After the epoxy material has cured, the experimentals and controls are scored in the center of the dish using a synthetic abrasive pad 2" in diameter mounted in a drill. Epoxy dust is removed by washing with distilled water. Dishes are allowed to dry and are used in the test three days after epoxy dust removal. The epoxy surface is abraded for several reasons:

1. Rough surface simulates in use effect of people walking constantly over a floor surface, and is a worst-case scenario for a coating.
2. Abraded surface provides attachment sites for microorganisms as would occur on a floor.
3. Diameter of the rough surface gives a surface area of 3.14 sq. in. (89.5 mm²). This allows for more accurate calculations of organisms per sq. in. (mm²) on the test material.
4. By having a central, specified area on the epoxy, contact with the sides of the dish not covered with epoxy are avoided during inoculation and recovery operations, thus preventing the intrusion of organisms not in the test area.
5. In this test, a rough surface is also necessary to prevent "beading-up" of the water based inoculum, thus preventing alteration of the relationship of organisms per square inch during the period of testing.

Organism preparation and inoculation of plates:

1. Cultures are prepared from 24 hour nutrient broth cultures of bacterial organisms by standard laboratory methods using centrifugation and resuspension in 0.85% NaCl.
2. Samples are removed and diluted into a 45° C. agar solution to yield a final count of organisms between $1\times10^4$ and $5\times10^4$ organisms/ml in a solution containing 0.85% saline and 0.3% agar (no organic nutrients).
3. Prewet abraded area of epoxy with 0.85% saline using a sterile cotton swab that has been dipped into sterile saline.
4. Pipette 0.1 ml of innoculum onto the center of the abraded area of the epoxy in the petri dishes.
5. Spread the inoculum over the entire abraded surface of the epoxy.
6. Following inoculation of all plates, immediately place plates top side down into a humidity chamber held at 18°-20° C. and a relative humidity in excess of 85%. Incubate for 30 hours and count viable organisms.

|  | CFU:sample | control | % reduction |
|---|---|---|---|
| With carrier+: |  |  |  |
| Staphylococcus | 0 | $1.0\times10^6$ | 100.0 |
| Psuedomonas | $3.9\times10^2$ | $2.8\times10^5$ | 99.9 |
| E. coli | $4.3\times10^3$ | $5.2\times10^6$ | 99.9 |
| Without carrier*: |  |  |  |
| Staphylococcus | $7.16\times10^4$ | $2.11\times10^6$ | 96.6 |
| Psuedomonas | $5.29\times10^4$ | $8.7\times10^4$ | 39.2 |
| E. coli | ND | ND | ND |

+Sample prepare above from mixture containing WC-8 as the diluent.
*The same relative quantity of phosphate ester salt was incorporated into an epoxy formed by mixing the combination of DER 331, DER 732, Dehydran 1208 and phosphate ester salt with Epotuf 37-606.

The samples with carrier retained their activity after repeated washings and scarifications, unlike the phosphate ester salt-epoxy mixture without carrier.

Modifications and variations of the claimed invention, biocidal phosphate ester-carrier delivery systems, will be obvious to those skilled in the art from the foregoing detailed description of the invention. These modifications and variations are intended to come within the scope of the appended claims.

We claim:

1. A biocidal composition comprising
   (a) an inert carrier wherein the carrier is a synthetic or natural polymer selected from the group consisting of proteins, polysaccharides, hydrocarbon polymers, and derivatives thereof and
   (b) a biocidally effective amount of a phosphate ester having the general formula:

$$\begin{array}{c} O \\ \parallel \\ HO-P-OR \\ | \\ OR' \end{array}$$

wherein R and R' are selected from the group consisting of alkyl, aryl, aralkyl and alkaryl groups, one of R or R' can be H, and there is at least one free hydroxyl group, and
the phosphate ester is bound to the carrier.

2. The biocidal composition of claim 1 wherein the phosphate ester is a partially neutralized acid having the general formula $$X^+ \quad \begin{array}{c} O \\ \parallel \\ {}^-O-P-OR \\ | \\ OH \end{array}$$

and X is selected from the group consisting of organic ions, Group IA metals, Group IIA metals and transition metals.

3. The biocidal composition of claim 2 wherein $X^+$ is an ammonium ion.

4. The biocidal composition of claim 3 wherein the ammonium ion has the general formula $$\begin{array}{c} R_1 \\ | \\ R_2-N^+-H \\ | \\ R_1 \end{array}$$

wherein $R_1$ is selected from the group consisting of an alkyl group of between 1 to 18 carbon atoms and a hydroxy alkyl group of from 2 to 18 carbon atoms; and $R_2$ is an alkyl group of from 8 to 18 carbons.

5. A biocidal composition comprising
   (a) an inert, inorganic particulate carrier selected from the group consisting of diatomaceous earth, attapulgite clay, colloidal silica and zeolite, and
   (b) a biocidally effective amount of a partially neutralized acid of a phosphate ester having the general formula:

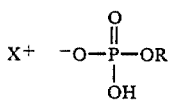

wherein R is selected from the group consisting of alkyl, aryl, aralkyl, alkaryl groups, and H, and there is at least one free hydroxyl group, and X is selected from the group consisting of organic ions, Group IA metals, Group IIA metals and transition metals, and the phosphate ester is bound to the carrier.

6. The biocidal composition of claim 5 wherein $X^+$ is an ammonium ion.

7. The biocidal composition of claim 1 wherein the carrier is a natural polymer selected from the group consisting of cotton, wool, linen, collagen, chitin, chitosan, and gelatin.

8. The biocidal composition of claim 1 wherein the carrier is selected from the group consisting of polyolefins, polystyrenes, polyamines, polyacrylics, polyamides, polyethers, polyurethanes, and monomers thereof.

9. The biocidal composition of claim 1 further comprising a buffering agent.

10. A method for manufacturing an article having antimicrobial properties comprising
   providing a biocidal composition wherein the biocidal agent consists of a phosphate agent including
   (a) an inert carrier and
   (b) a biocidally effective amount of a phosphate ester having the general formula:

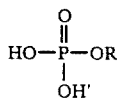

wherein R and R' are selected from the group consisting of alkyl, aryl, aralkyl and alkaryl groups, one of R or R' can be H, and there is at least one free hydroxyl group, and wherein the phosphate ester is bound to the carrier.

11. The method of claim 10 wherein the phosphate ester is a partially neutralized acid having the general formula

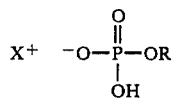

and X is selected from the group consisting of organic ions, Group IA metals, Group IIA metals and transition metals.

12. The method of claim 11 wherein X is an ammonium ion.

13. The method of claim 12 wherein the ammonium ion has the general formula

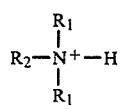

wherein $R_1$ is selected from the group consisting of an alkyl group of between 1 to 18 carbon atoms and a hydroxy alkyl group of from 2 to 18 carbon atoms; and $R_2$ is an alkyl group of from 8 to 18 carbons.

14. The method of claim 10 wherein the carrier is an inert, inorganic particulate selected from the group consisting of diatomaceous earth, attapulgite clay, colloidal silica and zeolite.

15. The method of claim 10 wherein the carrier is a synthetic or natural polymer selected from the group consisting of proteins, polysaccharides, hydrocarbon polymers, and derivatives thereof.

16. The method of claim 10 wherein the carrier is a natural polymer selected from the group consisting of cotton, wool, linen, collagen, chitin, chitosan, and gelatin.

17. The method of claim 10 wherein the carrier is a selected from the group consisting of polyolefins, polystyrenes, polyamines, polyacrylics, polyamides, polyethers, polyurethanes, and monomers thereof.

18. The method of claim 10 further comprising providing a buffering agent.

19. The method of claim 10 further comprising forming a coating of the carrier-biocidal composition.

20. The method of claim 10 further comprising microencapsulating the biocidal phosphate compound within the carrier.

21. The method of claim 10 further comprising adding the carrier-biocidal phosphate composition to a paint.

22. The biocidal composition of claim 6 wherein the ammonium ion has the general formula

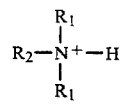

wherein $R_1$ is selected from the group consisting of an alkyl group of between 1 to 18 carbon atoms and a hydroxy alkyl group of from 1 to 18 carbon atoms; and $R_2$ is an alkyl group of from 8 to 18 carbons.

* * * * *